US00PP18004P3

(12) United States Plant Patent
Eppich

(10) Patent No.: US PP18,004 P3
(45) Date of Patent: Sep. 11, 2007

(54) APPLE TREE, 'EPPICH 2'

(50) Latin Name: *Malus pumila Mil*
Varietal Denomination: Eppich 2

(76) Inventor: Karl Eppich, 14480 Road 170, Mesa, WA (US) 99343

( * ) Notice: Subject to any disclaimer, the term of this patent is extended or adjusted under 35 U.S.C. 154(b) by 0 days.

(21) Appl. No.: 11/257,638

(22) Filed: Oct. 25, 2005

(65) Prior Publication Data

US 2007/0094759 P1 Apr. 26, 2007

(51) Int. Cl.
*A01H 5/00* (2006.01)

(52) U.S. Cl. ..... Plt./168

(58) Field of Classification Search ..... Plt./168
See application file for complete search history.

*Primary Examiner*—Kent Bell
*Assistant Examiner*—June Hwu
(74) *Attorney, Agent, or Firm*—Wells St. John PS.

(57) ABSTRACT

A new and distinct variety of apple tree is described, and which is characterized as to novelty by producing fruit having a brilliant red color, increased fruit pressure, increased brix, and further having a harvesting date about September 8, under the ecological conditions prevailing near Mesa, Wash.

4 Drawing Sheets

BACKGROUND OF THE NEW VARIETY

The present invention relates to a new and distinct variety of apple tree, *Malus pumila Mil* and which is named 'Eppich 2,' and more particularly to an apple tree which bears an attractive, brilliant red colored fruit, and which is further ripe for harvesting and shipment about September 8$^{th}$ under the ecological conditions prevailing near Mesa, Wash.

ORIGIN AND ASEXUAL REPRODUCTION

It has long been recognized that an important factor contributing to the success of any new variety of apple tree *Malus pumila Mil* bearing fruit for the fresh market is its respective date of harvesting in relative comparison to other varieties bearing similar fruit in the same season. Similarly, another significant factor effecting the commercial viability of any new strain of apple relates to its appearance, as well as its storage characteristics as reflected by such pomological characteristics as the starch level, and fruit pressure of same.

The new variety 'Eppich 2' is noteworthy in producing an attractively colored fruit which is ripe for harvesting and shipment at approximately September 8$^{th}$ under the ecological conditions prevailing near Mesa, Wash. Further, this new tree produces a fruit which has excellent storage starch levels and increased fruit pressure and brix in relative comparison to the variety its most closely similar to.

The new variety of apple tree *Malus pumila Mil* was discovered as a whole tree mutation within the cultivated area of a 'TAC 114 Fuji' orchard (U.S. Plant Pat. No. 8,032) which is located near Mesa, Wash. The inventor noticed the promising characteristics of this whole tree mutation in 1998. Thereafter, the inventor observed the tree for several additional years, and thereafter, in 2001, asexually reproduced the tree by budding the same tree over to test trees then planted at a commercial orchard located near Mesa, Wash.

These test trees have been subsequently studied and observed and its been determined that the same desirable characteristics observed in the original whole tree mutation were expressed in these same test trees. Additionally, the fruit produced from these same trees have been compared and contrasted with the fruit produced by 'TAC 114 Fuji' apple trees growing in the same orchard where the original whole tree mutation was discovered. It has been confirmed that these earlier asexual reproductions resulted in apple trees which posses the same distinctive characteristics as the original whole tree mutation.

SUMMARY OF THE VARIETY

The 'Eppich 2' apple tree is characterized by principally as to novelty by producing an attractively colored fruit which is ripe for harvesting and shipment approximately September 3$^{rd}$ — September 12$^{th}$ under the ecological conditions prevailing near Mesa, in the south central portion of Washington State. The present variety also displays excellent storage starch levels, increased fruit pressure and brix, as well as increased fruit weight in relative comparison to the fruit produced by the 'TAC 144 Fuji' apple tree (U.S. Plant Pat. No. 8,032) at the same geographical location.

BRIEF DESCRIPTION OF THE DRAWINGS

The accompanying drawings are color photographs of the present variety.

Figure 1:
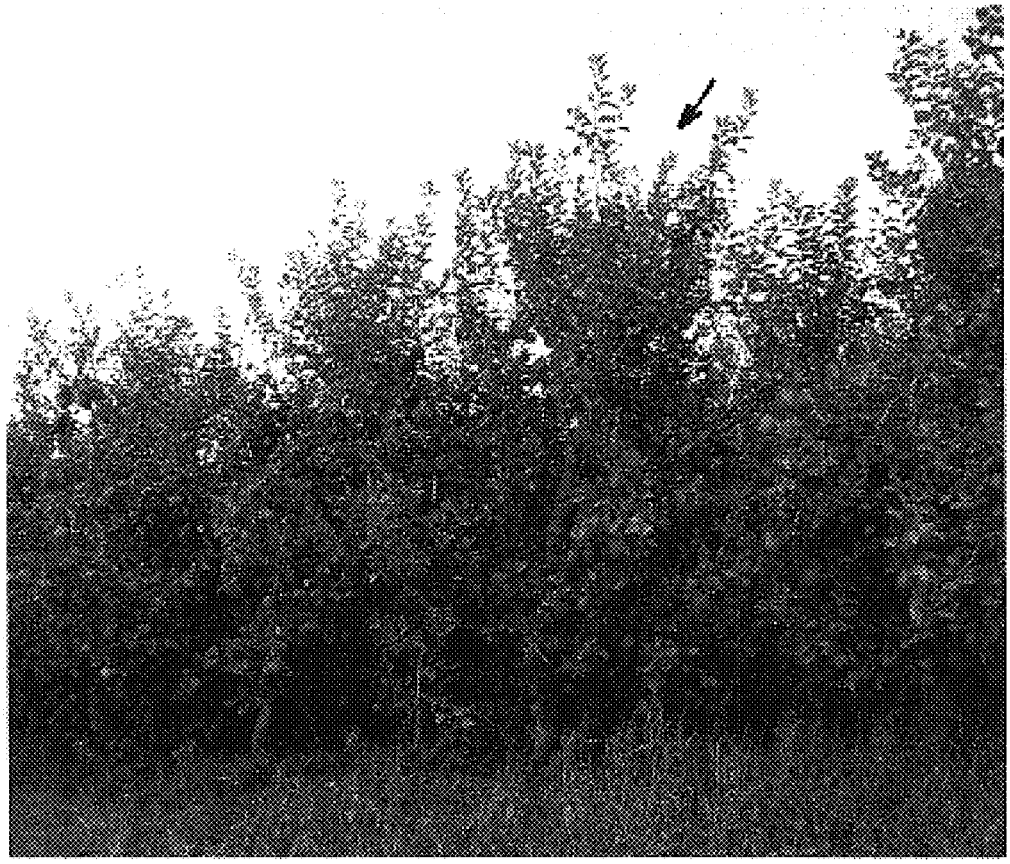
FIG. 1 illustrates the original whole tree mutation as seen growing in an orchard of TAC 114 Fuji apple trees (U.S. Plant Pat. No. 8,032) which is growing near Mesa, Wash.
Figure 2:
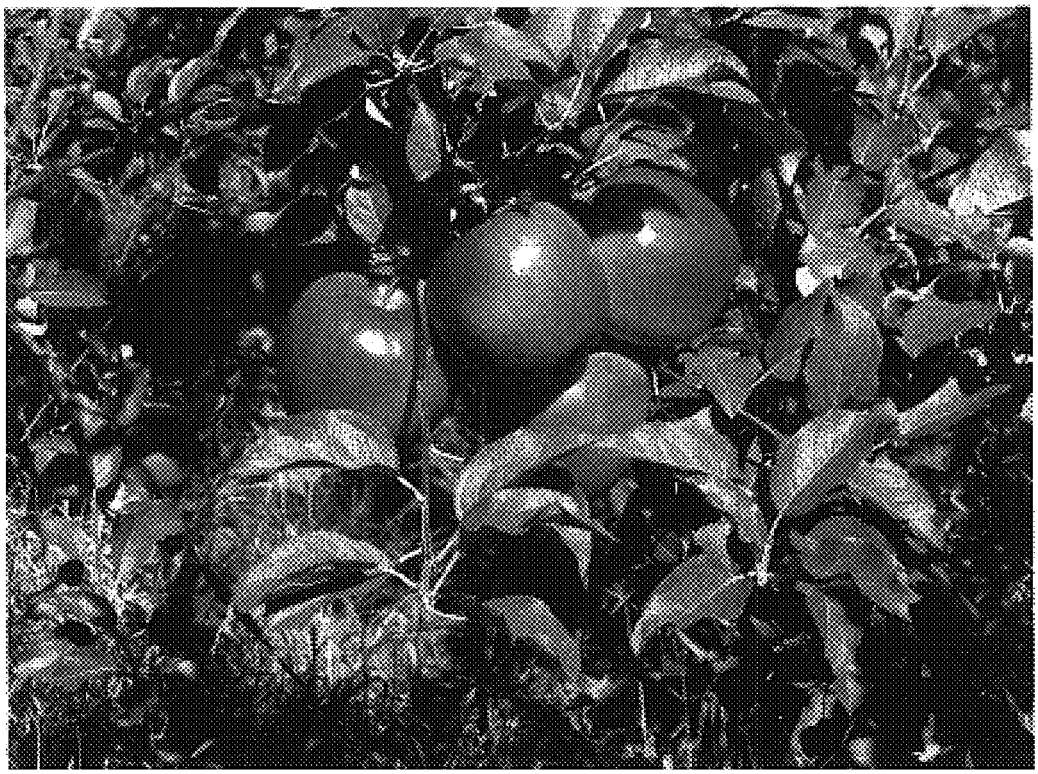
FIG. 2 shows the growth habit of the 'Eppich 2' apple tree.
Figure 3:
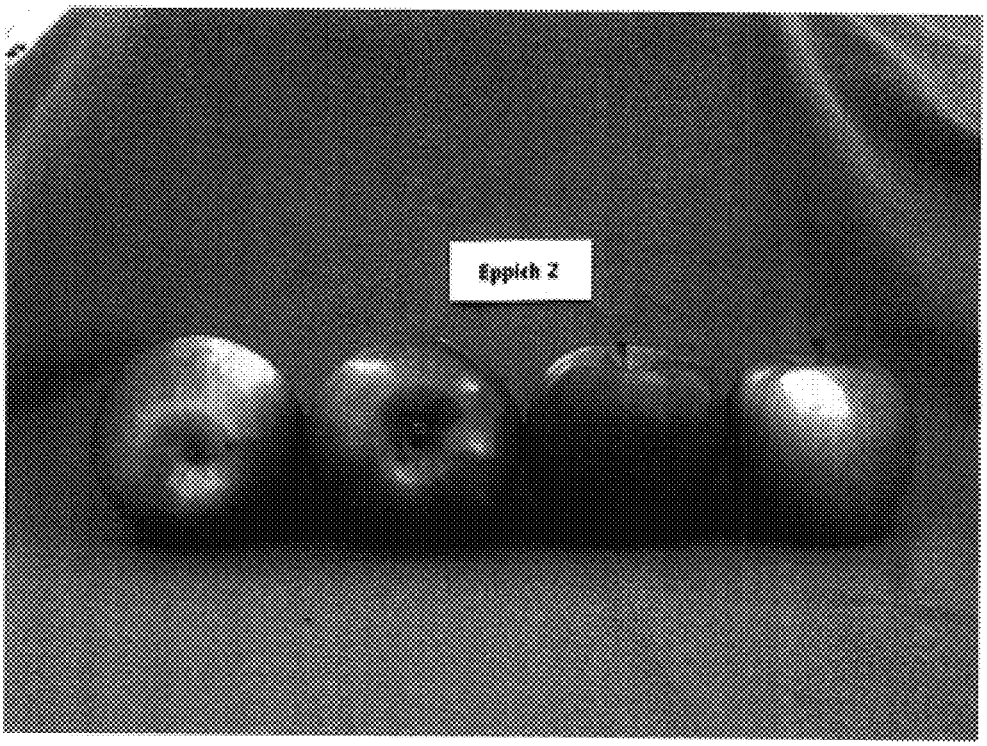
FIG. 3 shows four fruit of the present variety showing the exterior skin coloration sufficiently matured for harvesting and shipment.
Figure 4:
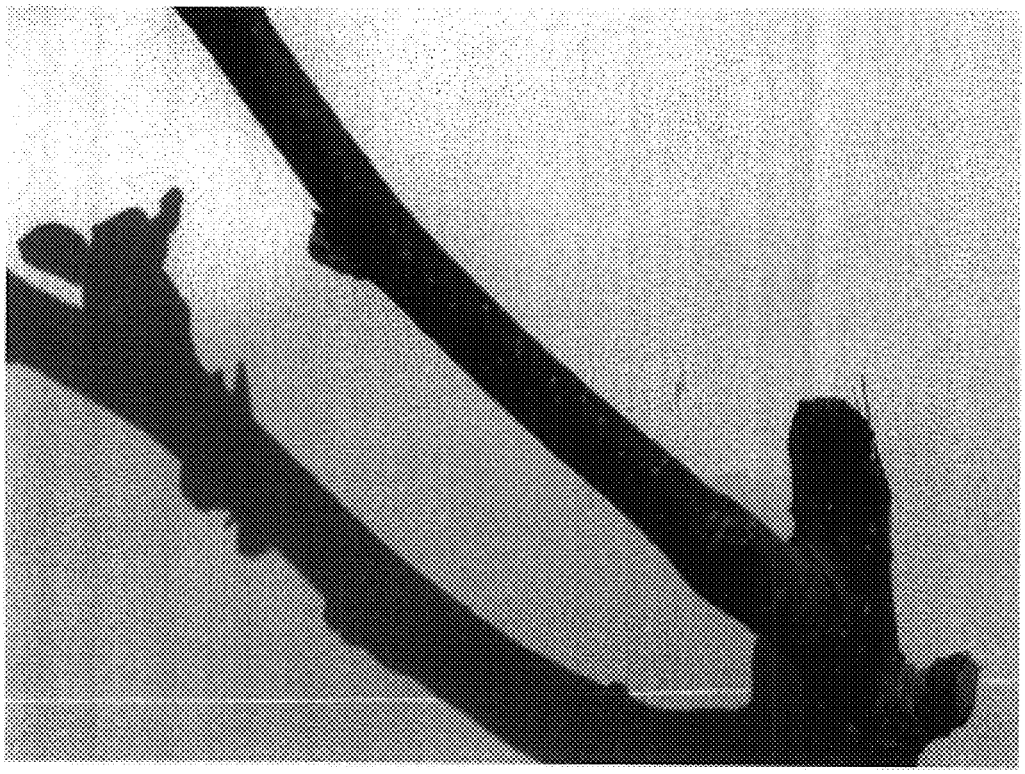
FIG. 4 shows the lenticel growth characteristics of the present variety as displayed on one year old wood.

The colors in the enclosed photographs are as nearly true as is reasonably possible in color photographs of this type. However, due to chemical development, processing and printing, the leaves and fruit depicted in these photographs may or may not be accurate when compared to the actual botanical specimens. For this reason, future color references should be made to the color plates (Royal Horticulture Society) and descriptions provided hereinafter.

DETAILED DESCRIPTION

Referring more specifically to the pomological details of this new and distinct variety of apple tree, the following has been observed under the ecological conditions prevailing at a test orchard which is located near Mesa, Wash. The major color code designations are by reference to The Royal Horticultural Society Colour Chart, London, 1996, common color names are also employed occasionally.

TREE

Size. — Generally — Average as compared to other apple cultivars growing under similar ecological conditions. The observed tree was planted in 1996 and was 9 years old. Height — 4.6 meters. Width — 3.7 mm.

Figure. — Upright to upright spreading in form.

Vigor. — Moderate.

Productivity. — Considered productive. The present variety shows a propensity for bi-annual bearing following a heavy crop year. Productivity is dependent upon cultural practices and therefore this aspect is not particularly distinctive of the variety.

Trunk. — Generally — Considered stocky and similar to the 'TAC 144 Fuji' apple tree from which it was derived as a whole tree mutation.

Surface texture. — Smooth and similar to that of the 'TAC 114 Fuji' apple tree.

Bark Color. — Gray Brown (197A). this is in contrast to the 'TAC 114 Fuji' apple tree which produces a bark color which is gray-grown (199D).

Branches. — Size — Generally average as compared to other apple cultivars. Branches. — Surface texture — Considered smooth. Branches. — Length — About 41.3 cm to about 66.7 cm. Branches. — Diameter — When measured at the first node, about 0.5 to about 0.8 cm. Internodes. — Length. — As measured between the $5^{th}$ and $6^{th}$ nodes, about 3.2 cm to about 5.1 cm.

Growth habit. — Generally considered spreading and moderately heavy in amount. The branches typically have wide angles. As a general matter branching on the 'Eppich 2' apple tree is moderate to moderately heavy on two year old wood. This is mostly fruiting spurs. In contrast, the branching habit of the 'TAC 114 Fuji' apple tree with which it is most closely similar, is moderate with few fruiting spurs on two year old wood.

Bark color. — 1 year old wood — Gray-orange (166A). In contrast, the bark color of the 'TAC 114 Fuji' apple tree has a gray-orange bark color which is most accurately characterized as a (177A).

Lenticels. — Shape — On 1 years old wood, these are considered small and round. In relative comparison to the 'TAC 114 Fuji' apple tree, the lenticels observed on same are generally twice as large, and are elongated on the same age of wood.

Regularly of bearing — Regular. Further, the present variety is considered hardy under the ecological conditions prevailing near Mesa, Wash.

LEAVES

Size. — Average as compared to other common varieties.

Leaf shape. — Considered broadly acute and mostly serrate with some bi-serrate.

Top surface texture. — Generally — The top surface is green (144A) and shiny. Further, the leaves may display an undulating surface with some upwardly folding of the sides.

Bottom surface texture. — Considered pubescent and similar in appearance to that of the 'TAC 114 Fuji' apple tree.

Mid-Rib. — Shape — Straight to slightly curved on both the present variety and the 'TAC 114 Fuji' apple tree.

Leaf length. — About 8.3 centimeters. This is in contrast to the 'TAC 114 Fuji' apple tree which, on average, produces a leaf length of about 8.99 centimeters.

Leaf width. — About 5.64 centimeters. This is in contrast to the leaf width of the 'TAC 114 Fuji' apple tree which is about 6.13 centimeters.

Petiole length. — About 3.35 centimeters. This is in contrast to the 'TAC 114 Fuji' apple tree which as a petiole length of about 2.92 centimeters. Petiole. — Color — Green (RHS 134D).

Stipule length. — About 0.9 centimeters. This is in contrast to the 'TAC 114 Fuji' apple tree that, on average, has a stipule length of about 1.05 centimeters. Stipule. — Color — Green (RHS 134C).

FLOWERS

Bloom time. — Considered midseason as compared to other apple varieties growing in south center Washington. The present variety had an observed bloom date of Apr. $7^{th}$ - $15^{th}$, 2005 under the ecological conditions prevailing near Mesa, Wash.

Petals. — Color — While (N-155D) and having highlights which appear red-purpled, and most accurately identified as (70B). This color is similar to the petal colors produced by the 'TAC 114 Fuji' apple tree.

Petals. — Size — About 16-19 millimeters long; and about 11-14 millimeters in width. This petal size is in contrast to that produced by the 'TAC 114 Fuji' apple tree which has a petal size of about 13 to about 15 millimeters in width; and about 18-20 millimeters in length. Petal Arrangement. — The flower petal arrangement is considered free when fully expanded.

Stamens. — Length — About 8-11 millimeters. This is in contrast to the 'TAC 114 Fuji' apple tree which has a stamen length of about 6 to about 9 millimeters.

Anthers. — Length — About 2.5 millimeters. In contrast the anthers found on the 'TAC 114 Fuji' apple tree have a length of about 2.5 to about 3 millimeters.

Pistil. — Length — About 5 to about 9 millimeters. This is in contrast to the pistil length as found on the 'TAC 114 Fuji' apple tree which is about 6 to about 10 millimeters in length.

Sepals. — Length — About 6 millimeters. This is in contrast to the sepals found on the 'TAC 114 Fuji' apple tree which are about 7 millimeters.

Sepals. — Form —form — At bloom, they are considered pubescent and curled downwardly. This growth habit does not appear distinctive of the present variety. Sepals. — Color — Green (RHS 134D) and having a reddish purple tip (RHS 71D).

FRUIT

Size. — Generally speaking, the fruit is considered medium to large for the variety. On average, the present variety is about 8.2 cm. in diameter and 7.4 cm. in height. This is in contrast to the fruit produced by the 'TAC 114 Fuji' apple tree at the same geographical location which has an average diameter of about 3.02 inches.

Fruit form. — Generally — Considered mostly round, although some round and conical forms may be found. In contrast, the 'TAC 114 Fuji' apple tree produces mostly round fruit.

Fruit cavity. — Average Width — About 3.97 centimeters. This is in contrast to the fruit produced by the 'TAC 114 Fuji' apple tree which has a fruit cavity of about 3.40 centimeters.

Fruit cavity. — Average depth — About 1.87 centimeters. This is in contrast to the fruit of the 'TAC 114 Fuji' apple tree which produces fruit cavity depth of about 1.65 centimeters.

Fruit eye. — Generally — having a reflexed tip. This is in contrast to the 'TAC 114 Fuji' apple tree which has a mostly erect convergent form, although some divergent forms may also be found.

Stem length. — About 2.25 centimeters. The fruit stems observed on the 'TAC 114 Fuji' apple tree has an average stem length of about 2.1 centimeters. Stem Color. — Green (RHS 134D).

Skin. — Overall appearance — Smooth and distinct. The skin is not greasy at harvest maturity.

Lenticels. — Numbers — Moderate in number and distinct. The lenticels are larger in size than that produced on the 'TAC 114 Fuji' apple tree. In this regard, the lenticels are about 0.3 to about 1 millimeter in diameter and flattened in form. In contrast, the 'TAC 114 Fuji' apple tree produces fruit which have numerous lenticels. Further, these same lenticels have an average size of about 0.1 to about 0.3 millimeters.

Skin color. — Generally — Considered highly colored and blushed with a very light stripe. In this regard, the over color is located on about 80% to 90% of the surface area and is in the red group (45C to about 47B); and the ground color is located on about 10% to 20% of the surface area and is in the yellow group of about (5C). In contrast, the fruit produced by the 'TAC 114 Fuji' apple tree is considered blushed with an over color of about (46B) and a ground color of about (5B). Bloom. — Generally — Present, but very light.

Flesh color . — White (155D).

Brix. — The average brix of the present variety is about 15.2. This is in contrast to the brix produced by the fruit of the 'TAC 114 Fuji' apple tree which is about 12.8.

Fruit pressure. — On average, the present variety has a fruit pressure of about 17.1. In contrast, the fruit pressure observed in the fruit of the 'TAC 114 Fuji' apple tree is about 15.9. The fruit is considered firm, crisp and juicy.

Starch index rating. — On average, about 3.4. This is in contrast to the starch rating of the fruit of the 'TAC 114 Fuji' apple tree which is about 4.3.

Aroma. — Generally — Considered moderately strong and distinct.

Core line. — Considered medium for the variety. This is in contrast to the fruit of the 'TAC 114 Fuji' apple tree which is considered basal and clasping.

Core position. — Generally speaking it considered distant. In contrast, in the fruit of the 'TAC 114 Fuji' apple tree, the core portion is considered medium to distant.

Cell. — Form — Considered tufted.

Cell. — Shape — Considered round.

Seeds. — Numbers — As many as 2. In contrast, the fruit of the 'TAC 114 Fuji' apple tree may have as many as 3 seeds.

Seed. — Shape — Considered acute.

Seed color — Considered grey-orange (166A).

Tube cavity. — Shape — Funnel Shaped.

Sepals. — Surface Texture — When found on the fruit, they are considered downy.

Stamens. — Position — Considered median and above the core line.

Axis. — Generally speaking, it is considered axial and mostly closed. This is in contrast to the fruit produced by the 'TAC 114 Fuji' apple tree which is considered to be abiaxial and open.

Fruit basin. — Average width — About 3.78 centimeters. This is in contrast to the fruit produced by the 'TAC 114 Fuji' apple tree which has an average width of about 3.08 centimeters.

Fruit basin. — Average depth — About 1.53 centimeters. This is contrast to the fruit of the 'TAC 114 FUji' apple tree which has an average depth of about 1.10 centimeters. Fruit Locules — Generally — Considered axial and open.

Date of maturity when described ripe for harvesting and shipment about Sep. 8, 2004 under the ecological conditions prevailing near Mesa, Wash. This date may vary based upon the prevailing ecological conditions.

Pollination. — This characteristic is satisfied by other diploid stains which are blooming approximately during the same bloom period.

Eating quality. — Considered excellent and useful as a fresh dessert apple.

Although the new variety of apple tree herein denominated as 'Eppich 2' possesses the described characteristics when grown under the ecological conditions prevailing near Mesa, Wash., it is to be understood that variations of the usual magnitude and characteristics incident to changes in growing conditions, fertilization, pruning and pest control are to be expected.

Having thus described and illustrated my new variety of apple tree, what I claim is new, and desired to secure by Plant Letters Patent is:

1. A new and distinct variety of apple tree substantially as illustrated and described, and characterized as to novelty by producing a highly colored apple having an increased size, excellent storage starch levels, and increased fruit pressure as compared to the fruit produced by the 'TAC 114 Fuji' apple tree when grown under the ecological conditions prevailing near Mesa, Wash.

* * * * *

UNITED STATES PATENT AND TRADEMARK OFFICE

CERTIFICATE OF CORRECTION

PATENT NO. : PP 18,004 P3
APPLICATION NO. : 11/257638
DATED : September 11, 2007
INVENTOR(S) : Karl Eppich It is certified that error appears in the above-identified patent and that said Letters Patent is hereby corrected as shown below:

Column 2, line 7, replace “which posses” with --which possess--.

Column 2, line 11, replace “characterized by” with --characterized--.

Column 3, line 36, Bark Color, replace “this” with --This--. Also replace “gray-grown” with --gray brown--.

Column 3, line 58, Lenticels, replace “years” with --year--.

Column 3, line 63, Regularly of bearing, replace “Regularly” with --Regularity--.

Column 4, line 15, Petiole length, replace “which as a” with --which has a--.

Column 4, line 28, Bloom time, replace “south center” with --south central--.

Column 4, line 33, Petals, replace “While” with --White--.

Column 4, line 47, after Anthers. –Length– insert --Anthers – Width - About 1.5 millimeters.--.

Column 4, line 54, Sepals, replace “–Form– from –” with -- –Form– --.

Column 6, line 1, Core position, replace “it considered” with --it is considered--.

Column 6, line 20, Fruit Basin, replace “This is contrast” with --This is in contrast--. Also, replace “FUji apple” with --Fuji apple--.

Signed and Sealed this

Fifteenth Day of July, 2008

JON W. DUDAS
*Director of the United States Patent and Trademark Office*